United States Patent
Hasegawa et al.

[11] Patent Number: 5,972,539
[45] Date of Patent: Oct. 26, 1999

[54] FLAME-RETARDANT SOLID ELECTROLYTES

[75] Inventors: Jun Hasegawa, Herkinan; Hiromochi Muramatsu, Nagoya; Hirohiko Saito, Oobu; Michiyuki Kono, Osaka; Hirohito Komori, Kyoto, all of Japan

[73] Assignees: Denso Corporation, Kariya; Dai-Ichi Kogyo Seiyaku Co., Ltd., Kyoto, both of Japan

[21] Appl. No.: 08/912,787

[22] Filed: Aug. 18, 1997

[30] Foreign Application Priority Data

Aug. 19, 1996 [JP] Japan .................................. 8-217454
Jul. 23, 1997 [JP] Japan .................................. 9-197181

[51] Int. Cl.$^6$ .................................................. H01M 10/22
[52] U.S. Cl. ........................ 429/304; 429/306; 429/314; 429/324
[58] Field of Search .................................. 429/306, 314, 429/324

[56] References Cited

U.S. PATENT DOCUMENTS 5,436,090   7/1995   Kono et al. .

FOREIGN PATENT DOCUMENTS

| | | |
|---|---|---|
| 631339 | 12/1994 | European Pat. Off. . |
| 60-47372 | 3/1985 | Japan . |
| 238451 | 2/1990 | Japan . |
| 6203814 | 7/1994 | Japan . |
| 6283205 | 10/1994 | Japan . |
| 7-6787 | 1/1995 | Japan . |

OTHER PUBLICATIONS

M. Kono et al, "Synthesis of Polymer Electrolytes Based on Poly[2–(2–methoxyethoxy)ethyl glycidylether] and Their High Ionic Conductivity", Polymers for Advanced Technologies, vol. 4; Jun. 6, 1992; pp. 85–91.

K. Motogami et al, "A New Polymer Electrolyte Based on Polyglycidylether", Electrochimica Acta. vol. 37, No. 9, 1992; pp. 1725–1727.

*Primary Examiner*—Maria Nuzzolillo
*Assistant Examiner*—Angela J. Martin
*Attorney, Agent, or Firm*—Pillsbury Madison & Sutro LLP

[57] ABSTRACT

A flame retardant solid electrolyte comprising an ion conductive polymer matrix having moieties capable of imparting flame retardance to the polymer matrix and ether bonds in the molecule and an electrolyte salt dispersed in the polymer matrix. The flame retardant solid electrolyte may be one which comprises a non-ion-conductive polymer matrix and a liquid electrolyte consisting of an electrolyte salt dissolved in a solvent therefor, which is dispersed in the polymer matrix. The flame retardance-imparting moieties are derived from halogen or phosphorus-bearing compounds.

24 Claims, 1 Drawing Sheet

FLAME-RETARDANT SOLID ELECTROLYTES

BACKGROUND OF THE INVENTION

1. Field of the Invention

This invention relates to a solid electrolyte, and more particularly, to a flame-retardant solid electrolyte which is applicable to secondary cells which are high in energy density and safety.

2. Description of the Prior Art

There is a great demand for secondary cells which have a high energy density in order to realize small-size and lightweight portable appliances.

In order to lower environmental pollution ascribed to exhaust gases from automobiles, many attempts have been made to put electric vehicles into practice. However, to realize electric vehicles requires the development of cells which have an energy density higher than existing lead batteries.

Technical developments have now been made in order to obtain cells or batteries which have a high energy density. In the event that such a high energy density cell suffers short-circuiting, the high energy of the cell is discharged at one time. Hitherto, it is usual to avoid the problem caused by overcharging, overdischarging or external short-circuiting by use of an outside safety mechanism. However, where short-circuiting occurs in the inside of a cell, the outside safety mechanism does not work appropriately.

Accordingly, it becomes necessary to develop a safety cell which does not rely on an outside safety mechanism.

SUMMARY OF THE INVENTION

It is accordingly an object of the invention to provide a flame-retardant solid electrolyte which has significantly improved flame retardance and can realize a safety cell of high energy density.

According to one embodiment of the invention, there is provided a flame retardant solid electrolyte which comprises an ion conductive polymer matrix having moieties derived from a halogen or phosphorus-bearing compound and capable of imparting flame retardance to the polymer matrix, and an electrolyte salt dispersed in the polymer matrix.

The moiety capable of imparting flame retardance to the ion conductive polymer matrix should preferably be derived from at least one compound selected from compounds of the general formulas (1), (2) and (3):

$$(CH_2=CR_2COO)_nR_1 \qquad (1)$$

wherein $R_1$ represents a halogen-containing aliphatic hydrocarbon residue, a halogen-containing aromatic hydrocarbon residue, or R' $OR_1$', in which R' represents an aliphatic or aromatic hydrocarbon residue, and $R_1$' represents a halogen-containing aliphatic or aromatic hydrocarbon residue, $R_2$ represents H or $CH_3$, and n is an integer of 1 to 3;

$$(CH_2=CR_2COO)_n(R_3O)_mPO(OR_4)_{3-m} \qquad (2)$$

wherein $R_2$ has the same meaning as defined above and represents H or $CH_3$, $R_3$ represents an aliphatic or aromatic hydrocarbon residue, $R_4$ represents hydrogen, an aliphatic or aromatic hydrocarbon residue or a phosphorus-containing aliphatic or aromatic hydrocarbon residue, m is an integer of 1 to 3, and n is an integer of 1 to 3; and

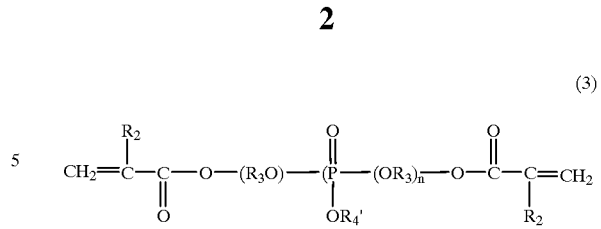

(3)

wherein $R_2$ has the same meaning as defined above and represents H or $CH_3$, $R_3$ has the same meaning as defined in (2) and represents an aliphatic or aromatic hydrocarbon residue, $R_4$' represents hydrogen, an aliphatic or aromatic hydrocarbon residue, or $-(R_3O)_{m'}-R_5$, in which $R_3$ is as defined above and represents an aliphatic or aromatic hydrocarbon residue, and $R_5$ represents hydrogen, or an aliphatic or aromatic hydrocarbon residue, and m' is an integer of from 0 to 20.

The ion conductive polymer matrix used in this embodiment should preferably be a crosslinked polymer product having a network structure obtained by crosslinking reaction between a homopolymer or copolymer (hereinafter referred to as polymer A) of alkylene oxides and/or glycidyl ethers, which is modified with polymerizable multiple bond groups at part or all of terminal end groups or functional groups in the polymer chain and the at least one compound selected from the compounds of the formulas (1), (2) and (3).

The electrolyte salt may be contained in the ion conductive polymer matrix in the form of a liquid electrolyte wherein an electrolyte salt is dissolved in an organic solvent. Such an organic solvent should preferably consist of at least one non-aqueous solvent selected from carbonates, lactones, ethers, sulfolanes, and dioxolanes.

The homopolymer or copolymer (polymer A) is modified to have a crosslinkable multiple bond group therein. Preferred examples of the crosslinkable multiple bond group include acrylic group, acryloyl, or methacryloyl.

The polymer A and at least one compound selected from those compounds of the general formula (1), (2) and (3) are preferably subjected to crosslinking reaction by application of actinic light such as an UV light, an electron beam or a gamma ray or the like, or by application of heat.

The electrolyte salts dispersed in the ion conductive polymer matrix should preferably include those salts of a lithium cation and one or more anions selected from those anions such as $BF_4$, $PF_6$, $ClO_4$, $AsF_6$, $CF_3SO_3$, $N(CF_3SO_2)_2$, $N(C_2F_5SO_2)_2$, $C(CF_3SO_2)_3$, and derivatives thereof.

It is preferred that the flame-retardant ion conductive polymer matrix is obtained by crosslinking reaction between the polymer A and at least one compound selected from those compounds of the general formulas (1), (2) and (3) at a ratio by weight of 40:60 to 98:2.

According to another embodiment of the invention, there is also provided a flame-retardant solid electrolyte which comprises a non-ion-conductive polymer matrix having moieties capable of imparting flame retardance thereto, and a liquid electrolyte wherein an electrolyte salt is dissolved in an organic solvent therefor.

The moieties capable of imparting flame retardance to the polymer should preferably be those derived from at least one compound selected from the compounds of the above-indicated general formulas (1), (2) and (3).

The non-ion-conductive polymer serving as a matrix of the solid electrolyte should preferably have a skeletal structure consisting of a polymer of at least one monomer selected from vinylidene chloride, acrylonitrile and methyl methacrylate.

At least one compound selected from those of the formulas (1), (2) and (3) are preferably present in the non-ion-conductive polymer matrix at a ratio by weight of 2 to 60%.

PREFERRED EMBODIMENTS OF THE INVENTION

Figure 1:
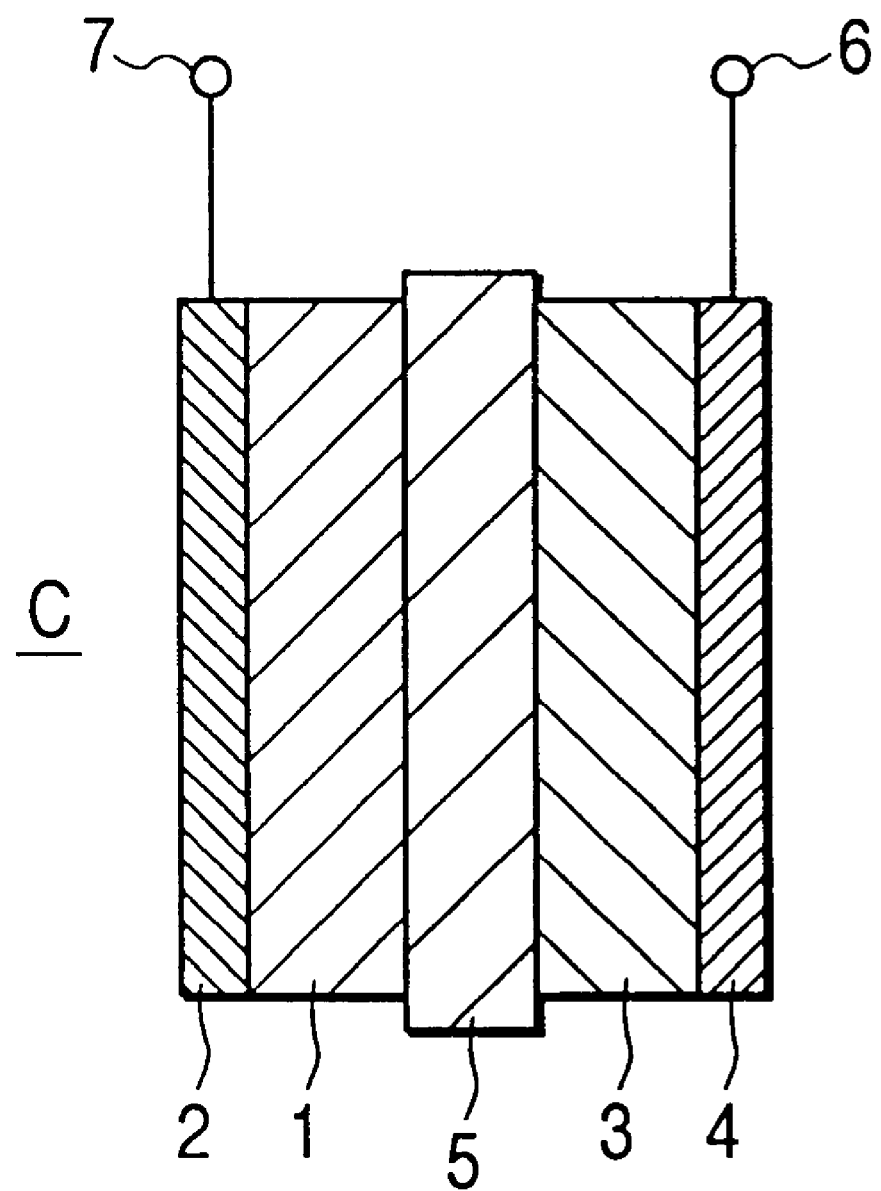
FIG. 1 is a schematic sectional view showing a lithium secondary cell using a flame-retardant solid electrolyte of the invention.

The solid electrolyte of the invention has a skeletal structure comprising moieties capable of imparting flame retardance to the structure and derived from at least one compound selected from those compounds of the general formula (1), (2) and (3). When using this type of flame-retardant solid electrolyte, a cell using the solid electrolyte is imparted with flame retardance, thereby enhancing the safety of the cell.

The flame-retardant solid electrolyte of the invention is not a mere mixture of a flame retardant and an ion conductive polymer, but is made of an ion conductive polymer wherein such functional groups or moieties capable of imparting flame retardance to the polymer are joined to the skeletal structure of the polymer. Accordingly, any free flame-retardant substance is not present in the ion conductive polymer, and thus, migration of such a flame-retardant substance through the polymer does not occur. This is advantageous in that a good flame-retardant effect can be expected throughout the polymer without involving any local loss of the effect. In the event that a cell using the solid electrolyte of the invention would be exposed to a solvent in the inside thereof, any flame retardant would not be dissolved out. Thus, the flame retardant effect of the polymer matrix is not lost.

According to one embodiment of the invention, the flame-retardant solid electrolyte should comprise an ion conductive polymer matrix having moieties derived from a halogen or phosphorus-bearing compound and capable of imparting flame retardance to the polymer matrix, and an electrolyte salt dispersed in the polymer matrix.

The polymer matrix should preferably consist of a crosslinked network product between a polymer of at least one compound selected from alkylene oxides and glycidyl ethers, which polymer is modified with a crosslinkable multiple bond group at part or all of terminal end groups and/or functional groups in the polymer chain, and at least one compound selected from compounds of the general formulas (1), (2) and (3)

(1)

wherein $R_1$ represents a halogen-containing aliphatic hydrocarbon residue, a halogen-containing aromatic hydrocarbon residue, or R' $OR_1$', in which R' represents an aliphatic or aromatic hydrocarbon residue, and $R_1$' represents a halogen-containing aliphatic or aromatic hydrocarbon residue, $R_2$ represents H or $CH_3$, and n is an integer of 1 to 3;

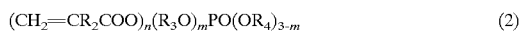

(2)

wherein $R_2$ has the same meaning as defined above and represents H or $CH_3$, $R_3$ represents an aliphatic or aromatic hydrocarbon residue, $R_4$ represents hydrogen, or an aliphatic or aromatic hydrocarbon residue or a phosphorus-containing aliphatic or aromatic hydrocarbon group, m is an integer of 1 to 3, and n is an integer of 1 to 3; and

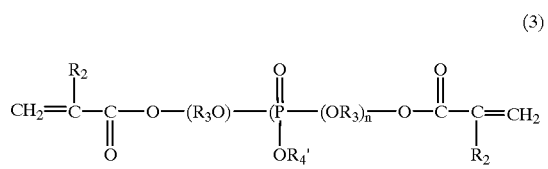

(3)

wherein $R_2$ has the same meaning as defined above and represents H or $CH_3$, $R_3$ has the same meaning as defined in (2) and represents an aliphatic or aromatic hydrocarbon residue, $R_4$' represents hydrogen, an aliphatic or aromatic hydrocarbon residue, or —$(R_3O)_{m'}$—$R_5$, in which $R_3$ is as defined above and represents an aliphatic or aromatic hydrocarbon residue, and $R_5$ represents hydrogen, or an aliphatic or aromatic hydrocarbon residue, and m' is an integer of from 0 to 20.

In the above formulas (1), (2) and (3), the halogen-containing aliphatic hydrocarbon residue represented by $R_1$ has from 1 to 10 carbon atoms and includes, for example, dibromopropyl, tribromoneopentyl and the like. Likewise, the halogen-containing aromatic hydrocarbon residue represented by $R_1$ includes, for example, tribromophenyl, dibromotolyl and the like. The aliphatic residue or group represented by R' has from 1 to 30 carbon atoms, preferably from 1 to 10 carbon atoms and includes, for example, methyl, ethyl, propyl, butyl, pentyl, hexyl, heptyl, octyl, nonyl, decyl and the like. The aromatic group represented by R' includes, for example, phenyl, tolyl or the like. The aliphatic moiety of the halogen-containing aliphatic hydrocarbon residue represented by $R_1$' has from 1 to 10 carbon atoms and includes, for example, methyl, ethyl, propyl, butyl, pentyl, hexyl, heptyl, octyl, nonyl, decyl and the like, and methylene and ethylene. The aromatic moiety of the halogen-containing aliphatic hydrocarbon residue represented by $R_1$' includes, for example, phenyl, tolyl and the like. The aliphatic hydrocarbon residue represented by $R_3$ and $R_4$ has from 1 to 10 carbon atoms and includes, for example, methyl, ethyl, propyl, butyl, pentyl, hexyl, heptyl, octyl, nonyl, decyl and the like. The aromatic hydrocarbon residue represented by $R_3$ and $R_4$ includes, for example, phenyl, tolyl or the like. The aliphatic moiety of the phosphorus-containing aliphatic hydrocarbon residue represented by $R_4$ has from 1 to 10 carbon atoms as defined with respect to $R_3$. The aromatic moiety of the phosphorus-containing aliphatic hydrocarbon residue represented by $R_4$ includes, for example, phenyl, tolyl or the like.

The aliphatic or aromatic hydrocarbon residues represented by $R_4$' and $R_5$ are, respectively, those defined with respect to $R_3$ or $R_4$.

As defined before, n is an integer of from 1 to 3, and m is an integer of from 1 to 3. m' in the formula (3) is an integer of from 0 to 20, preferably 0 to 3.

Specific and preferred examples of the compound represented by the general formula (1) include halogen-containing compounds indicated below:

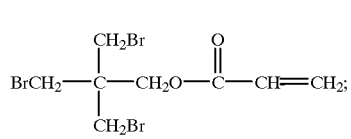 (I)
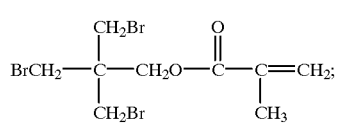 (II)
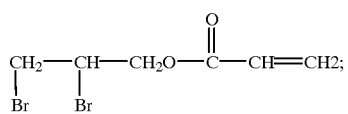 (III)
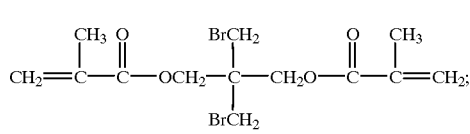 (IV)
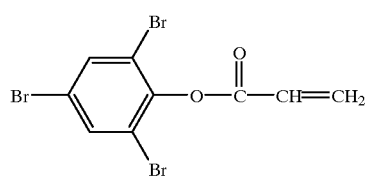 (V)
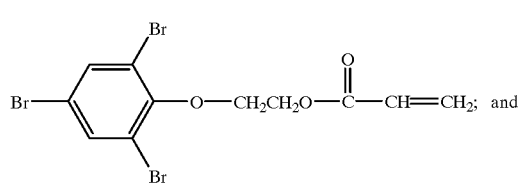 (VI)
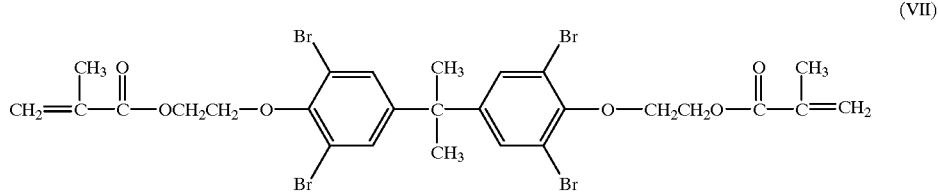 (VII)
Specific and preferred examples of the phosphorus-containing compounds of the formulas (2) and (3) are those indicated below:
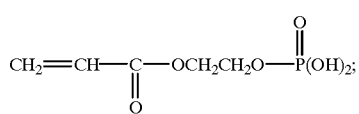 (VIII)
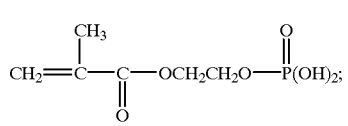 (IX)
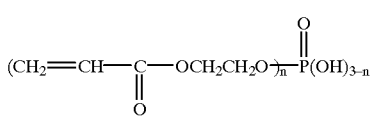 (X)
wherein n is 1 or 2;
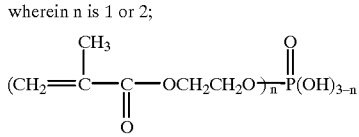 (XI)
wherein n is 1 or 2;

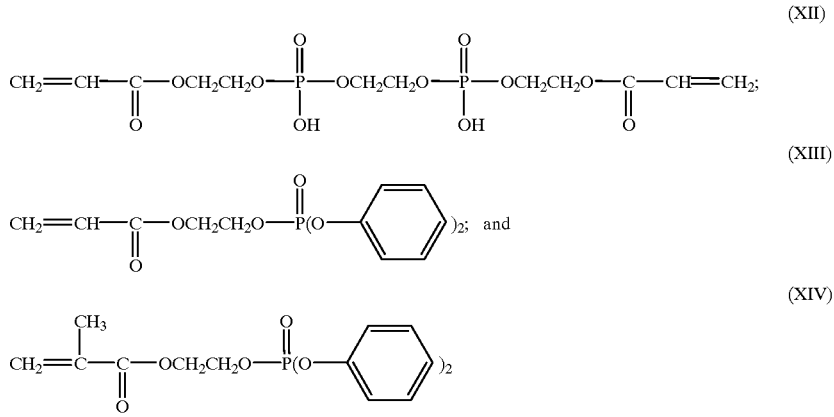

The other component for the ion conductive polymer is made of a homopolymer or copolymer of alkylene oxides and/or glycidyl ethers. The homopolymer or copolymer should be modified with a crosslinkable multiple bond group at part or all of the terminal end groups and/or functional groups in the chain thereof.

Examples of such a homopolymer or copolymer include those represented by the following general formula (4)

$$Z\{(CH_2CH_2O)_o(CH_2CHR_6O)_p\}_q Y \qquad (4)$$

wherein $R_6$ represents an alkyl group having from 1 to 12 carbon atoms, an alkenyl group having from 1 to 12 carbon atoms, or a group of the formula, $CH_2OReRa$ in which Ra represents an alkyl or alkenyl group having from 1 to 4 carbon atoms, and Re represents $(CH_2CH_2O)_k$ wherein k is an integer of 0 to 10, Y represents an alkyl or alkenyl group having from 1 to 12 carbon atoms, an acrylic acid residue, a methacrylic acid residue, Z represents an active hydrogen-bearing compound residue, o is an integer of 0 to 1100, p is an integer of 0 to 850, and q is an integer of 1 to 3.

The active hydrogen-bearing compound residues are those derived from alcohols such as ethylene glycol, glycerol and the like and amines such as ethylenediamine, n-butylamine and the like. The molecular weight of the homopolymer or copolymer is preferably in the range of 200 to 50,000.

Glycidyl ether homopolymers may be prepared according to the following reaction formula

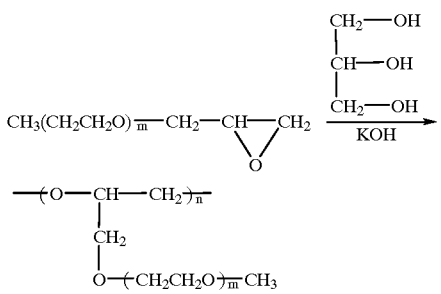

wherein m and n are, respectively, an integer.

(Ethylene oxide)-(glycidyl ether) copolymers may be prepared according to the following reaction formula

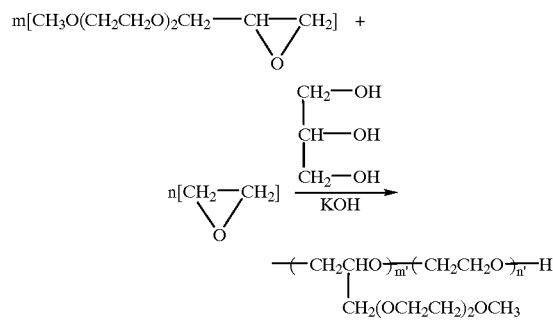

wherein m' and n' are, respectively, an integer.

Moreover, modified homopolymers or copolymers may be prepared according to a process described, for example, in U.S. Pat. No. 5,436,090, Electrochimica Acta, 37, 9, pp. 1725 (1992), and Polymers for Advanced Technology, 4. p. 179 (1993). For instance, a trifunctional terminal acryloyl-modified alkylene oxide polymer is prepared by a procedure wherein alkylene oxides are polymerized, for example, with glycerol or trimethylolpropane by ring-opening and the resultant polyalkylene oxide polymer is esterified with an unsaturated organic acid such as acrylic acid or methacrylic acid or is dehydrochlorinated with an acid chloride such as an acrylic chloride or methacrylic acid chloride.

Specific examples of the modified polymer or copolymer (polymer A) include alkylene oxide diacrylate having a molecular weight ranging from 500 to 5,000, (ethylene oxide-propylene oxide) random copolymer triacrylate having a molecular weight ranging from 3,000 to 20,000, (ethylene oxide-butylene oxide) random copolymer trimethacrylate having molecular weight of 3,000 to 30,000, those homopolymers and copolymers of the formulas mentioned above which are modified with acrylic acid or methacrylic acid, and the like.

In order to obtain a flame retardant solid electrolyte comprising an electrolyte salt dispersed or dissolved in the ion conductive polymer matrix in the form of ions, an electrolyte salt is mixed with the polymer A and a halogen or phosphorus-bearing compound selected, for example, from compounds of the afore-indicated general formulas (1), (2) and (3). Then, a crosslinking agent such as benzoyl peroxide is added to the resultant mixture, followed by heating at a temperature of 80 to 110° C. for 0.5 to 2 hours to obtain a crosslinked product having the electrolyte salt dispersed therein.

The polymer A has a multiple bond group, such as a vinyl group, and an ether bond in the molecule and can impart ion conductivity and polymeric physical properties to the ion conductive polymer. The polymer A having multiple bond groups and at least one compound having multiple bond groups selected from those compounds of the general formulas (1), (2) and (3) are crosslinked through both types of multiple bond groups. As a result, there can be formed a polymer matrix having both flame retardance and ion conductivity.

The ion conductive polymer should preferably be made of a crosslinked product obtained by reaction between the polymer A and at least one compound selected from the compounds of the general formulas (1), (2) and (3) at a ratio by weight of 40:60 to 98:2. If the ratio by weight of at least one compound imparting flame retardance is less than 2, flame retardance is not satisfactorily shown. On the contrary, when the ratio of at least one compound exceeds 60, the characteristic properties of the ion conductive polymer may unfavorably be lost.

Both polymer A and at least one compound selected from those compounds of the general formulas (1), (2) and (3) have multiple bond groups such as an acrylic acid group, an acryloyl group, a methacryloyl group and the like.

The electrolyte salts usable for this purpose include, for example, lithium borofluoride, lithium hexafluorophosphate, lithium perchlorate, lithium hexafluoroarsenate, lithium trifluoromethanesulfonate, lithium imides, lithium methides and derivatives thereof such as lithium trifluoromethanesulfonylimide, lithium trifluoromethanesulfonylmethide and the like, and mixtures thereof. These salts should preferably be present in the ion conductive polymer matrix in an amount of 2 to 20 wt % based on the polymer.

The solid electrolyte according to this embodiment may further comprise an organic solvent. In this case, an electrolyte salt is dissolved in a solvent thereof to provide a liquid electrolyte. Preferably, the liquid electrolyte has a concentration of 0.5 to 2 moles/liter. This liquid electrolyte is added to a mixture of the polymer A and a halogen or phosphorus-bearing compound, e.g. the compound selected from compounds of the formulas (1), (2) and (3), followed by crosslinking reaction by irradiation of UV light, an electron beam or a gamma ray, or by application of heat. As a matter of course, if UV light is used, photopolymerization initiators ordinarily used for this purpose may be used.

The resultant polymer is at least partially crosslinked, so that when the crosslinking reaction is conducted in co-existence of a relatively large amount of a liquid electrolyte, the resultant crosslinked product may be so formed as to be swelled in the liquid electrolyte. This type of solid electrolyte may be called a gel-type solid electrolyte.

The organic solvents used for this purpose include non-aqueous solvents such as carbonates, lactones, ethers, sulfolanes, dioxolanes and mixtures thereof. Specific examples include propylene carbonate, ethylene carbonate, dimethyl carbonate, diethyl carbonate, ethylmethyl carbonate, tetrahydrofuran, 2-methyltetrahydrofuran, γ-butyrolactone, 1,2-dimethoxyethane, diethoxyethane, 1,3-dioxolane, 1,3-dimethoxypropane and mixtures thereof.

The liquid electrolyte should preferably be present at a ratio by weight between the ion conductive polymer and the liquid electrolyte of 10:90 to 90:10.

According to another embodiment of the invention, the solid electrolyte may be made of a non-ion-conductive polymer matrix imparted with flame retardance, and a liquid electrolyte of an electrolyte salt in an organic solvent dispersed in the non-ion conductive polymer matrix. The liquid electrolyte should preferably be present at such a ratio as defined with respect to the first embodiment.

The non-ion conductive polymer matrix is made of a copolymer of at least one compound selected from those compounds of the afore-indicated formulas (1), (2) and (3) and at least one monomer selected from vinylidene chloride, acrylonitrile and methyl methacrylate. At least one compound should preferably present in an amount of 2 to 60 wt % and the balance is for the at least one monomer. The copolymerization is conducted by a usual manner such as suspension or solution polymerization.

The resultant copolymer has no ether bond exhibiting ion conductivity in the molecule. When the copolymerization is conducted in a medium comprising an organic solvent and a salt electrolyte or when a separately prepared non-ion-conductive polymer is heated in a liquid electrolyte, the liquid electrolyte is taken in and swells the polymer, thereby providing a flame retardant solid electrolyte or a gel-type solid electrolyte. The solid electrolyte can be used, like the electrolyte comprising the ion conductive polymer.

The types and amounts of organic solvents and salt electrolytes, and the amount of a liquid electrolyte are those described with respect to the first embodiment.

The flame retardant solid electrolytes of the invention can be used in lithium primary and secondary cells.

The application to a lithium secondary cell is descried below.

FIG. 1 shows a fundamental lithium secondary cell. In FIG. 1, there is shown a cell C having a negative electrode 1 and a positive electrode 3 sandwiching a solid electrolyte layer 5 therebetween. The negative electrode 1 has a current collector 2 therefor on the outer side thereof. Likewise, the positive electrode 3 has a current collector 4 therefor. Indicated by 6 and 7 are, respectively, terminals for the positive electrode 3 and the negative electrode 1.

The active substance of the negative electrode 1 consists of lithium or its alloy as ordinarily used for this purpose. Similarly, the active substance of the positive electrode 3 may be any ones known in the art, e.g. metal oxides such as nickel oxide, cobalt oxide, titanium oxide and the like, and metal sulfides such as molybdenum sulfide, iron sulfide and the like. The current collectors 2, 4 may be, respectively, made of a conductive material such as carbon, stainless steels, titanium, nickel, copper, gold or the like in the form of fibers, mesh or the like.

The solid electrolyte layer 5 is made of a flame retardant solid electrolyte according to the invention.

In operation, when the cell is discharged, lithium ions from the negative electrode active substance are electrochemically moved into the solid electrolyte layer 5. At the same time, lithium ions in the solid electrolyte layer 5 are taken in the active substance of the positive electrode 3. On the other hand, for the charge reaction, the lithium ions in the solid electrolyte deposits as lithium metal, and the lithium ions in the positive electrode active substance is unlikely to dissolve out in the solid electrolyte layer.

At the time of charging, when lithium deposited as lithium metal is not uniformly deposited on the surface of lithium but locally deposited, the locally deposited metal serves as a growing nucleus, from which lithium dendritically grows through the solid electrolyte. Finally, the resultant dendrite is in contact with the positive electrode, thereby causing short-circuiting of the cell. In this condition, a great current passes within a very short time, with the possibility that the cell catches fire.

In the practice of the invention, the ion conductive polymer matrix or the non-ion conductive polymer matrix contains halogen or phosphorus-bearing moieties capable of imparting flame retardance to the matrix. If a great current passes within a short time such as by short-circuiting, the polymer matrix can suppress the cell from catching fire.

When the negative electrode active substance is not made of lithium or its alloy but is made of a material capable of occlusion and discharge of lithium ions, e.g. a carbon material, lithium metal deposits on the carbon surface at the time of overcharge. This deposit serves as a growing nucleus to permit dendrite to grow, thereby causing short-circuiting. In this sense, the use of the ion conductive polymer or non-ion-conductive polymer is effective in improving the safety of the cell.

The invention is more particularly described by way of examples, which should not be construed as limiting the invention thereto.

EXAMPLE 1

An ion conductive polymer was prepared by providing alkylene oxide diacrylate serving polymer A having a molecular weight of 1000 and a bromine-bearing compound of the afore-indicated formula (III) at a mixing ratio by weight of 75:25. 70 wt % of a liquid electrolyte consisting of 1 mole/liter of $LiClO_4$ in propylene carbonate was added to 30 wt % of the mixture, to which 1000 ppm of a photopolymerization initiator, Irgacure 651 (Chiba-Geigy), was added. The resulting mixture was applied onto a positive electrode and then subjected to crosslinking reaction by irradiation of light with a wavelength of 365 nm from a UV lamp of 30 $mW/cm^2$ for 5 minutes in an atmosphere of an inert gas, thereby forming a solid electrolyte on the positive electrode although any other techniques of forming a solid electrolyte layer may be used.

The electric conductivity of the solid electrolyte was found to be $2\times10^{-3}$ S/cm. The flame retardance of the solid electrolyte was evaluated according to the UL-94 flame retardance test, revealing that the flame retardance corresponded to V-0.

In the flame retardance test, a test piece having a length of 125 mm, a width of 13 mm and a thickness of 3 to 13 mm was fixed vertically by means of a clamp by 6 mm from the above. Marking absorbent cotton was placed on a floor below the test piece in order to confirm whether or not the cotton was ignited by means of a dropped matter from the test piece. A burner was placed below the test piece at a distance of 10 mm from the lower end of the piece, followed by applying a flame at the center of the test piece for 10 seconds and then keeping the flame apart from the piece over 150 mm or above. An afterflame time, t1, was measured in seconds. Immediately after the afterflame ceased, the burner was again moved below the test piece and set at a distance of 10 mm from the residue of the piece for 10 seconds. Thereafter, the burner was kept apart from the piece at a distance of 150 mm or above. An afterflame time, t2, and an afterglow time, t3, were, respectively, measured.

The evaluation standards are as follows.
- 94 V-0: neither afterflame nor afterglow arrived at the clamp and no ignition of the absorbent cotton took place within a time, t1 or t2, of 10 seconds, within a total time of t1+t2 of 50 seconds, and within a total time of t2+t3 of 30 seconds.
- 94 V-1: neither afterflame nor afterglow arrived at the clamp and no ignition of the absorbent cotton took place within a time, t1 or t2, of 30 seconds, within a total time of t1+t2 of 250 seconds, and within a total time of t2+t3 of 60 seconds.
- 94 V-2: similar to the case of 94 V-1, but the absorbent cotton was ignited.

EXAMPLE 2

Poly(ethylene oxide-propylene oxide) random copolymer triacrylate having a ratio by weight between ethylene oxide and propylene oxide of 60:40 and a molecular weight of 6000 and a phosphorus-bearing compound of the afore-indicated formula (VI) were mixed at a ratio by weight of 80:20. 70 wt %, based on the mixture, of an electrolyte solution of 1 mole/liter of $LiPF_6$ in a mixed solvent of ethylene carbonate (EC) and dimethoxyethane (DME) at a ratio of 1:1 was added to 30 parts by weight of the mixture, followed by irradiation with an electron beam in an atmosphere of an inert gas to obtain a crosslinked product. The irradiation was conducted by use of an electron beam irradiator under conditions of an acceleration voltage of 150 kV and an electron beam dosage of 10 Mrad.

The resultant solid electrolyte was found to have a conductivity of $1\times10^{-3}$/cm. The flame retardance was evaluated in the same manner as in Example 1, revealing that the retardance corresponded to V-1.

EXAMPLE 3

Poly(ethylene oxide-butylene oxide) random copolymer trimethacrylate having a ratio by weight between ethylene oxide and propylene oxide of 90:10 and a molecular weight of 48000 and a bromine-bearing compound of the afore-indicated formula (III) were mixed at a ratio by weight of 60:40. one mole of a $LiPF_6$ supporting electrolyte alone was added to 1 kg of the mixture, to which 1 wt % of benzoyl peroxide serving as a crosslinking agent was added, followed by maintaining at 80° C. for 1 hour to obtain a crosslinked product.

The resultant solid electrolyte product was found to have a conductivity of $2\times10^{-5}$ S/cm. The flame retardance was evaluated in the same manner as in Example 1, revealing that the retardance corresponded to V-0.

COMPARATIVE EXAMPLE 1

The general procedure of Example 1 was repeated without addition of any bromine-bearing compound. The flame retardance of the resultant solid electrolyte was evaluated in the same manner as in Example 1, revealing the retardance did not pass the standard of V-2 and did not exhibit flame retardance.

EXAMPLE 4

Such starting components as used in Example 1 including the alkylene oxide diacrylate, the bromine-bearing compound, $LiClO_4$/propylene carbonate and the photopolymerization initiator were mixed, followed by impregnation in a sheet-shaped positive electrode made of $LiMn_2O_4$ and also in a sheet-shaped negative electrode made of a carbon material under reduced pressure. Thereafter, UV light was irradiated on the thus impregnated electrodes to obtain a positive electrode and a negative electrode each integrally combined with the flame retardant solid electrolyte. The sheet-shaped positive electrode, the solid electrolyte sheet obtained in Example 1 and the negative electrode were superposed in this order and convolutely wounded to obtain a cylindrical cell attached with a safety valve by a usual manner.

The ell was heated by means of a burner or heated with a hot plate, whereupon the safety valve worked but neither ignition nor bursting took place.

EXAMPLE 5

A flame retardant solid electrolyte composition of the type used in Example 3 was impregnated, under reduced pressure, in a cylindrical cell structure obtained by convolutely winding a sheet-shaped positive electrode, a separator made of a polypropylene non-woven fabric, and a sheet-shaped negative electrode and inserting the wound body into a casing, followed by heating to crosslink the electrolyte composition thereby obtaining a cell. The cell was heated by means of a burner, whereupon neither ignition nor bursting took place although a safety valve went into action.

COMPARATIVE EXAMPLE 2

Such a cylindrical cell structure as used in Example 5 was impregnated with a liquid electrolyte consisting of 1 mole/liter of $LiPF_3$ in a mixed solvent of ethylene carbonate and dimethoxyethane (DME) at a mixing ratio of 1:1 to obtain a cell. The thus obtained cell was heated by use of a burner, revealing that a safety valve worked and the cell took fire. Likewise, when the cell was heated on a hot plate, the safety valve worked, resulting in the ignition of the cell.

EXAMPLE 6

A compound of the afore-indicated formula (IV) and methyl methacrylate were mixed at a mixing ratio by weight of 25:75 and subjected to suspension polymerization in the presence of azobutyronitrile at a temperature of 50 to 100° C. for 3 hours to obtain a copolymer having a molecular weight of about 200,000 and Br-bearing moieties in the molecule. The copolymer was dissolved in methyl ethyl ketone, applied onto a glass sheet and dried to obtain about 30 $\mu$m thick film. The film was heated to 100° C. and immersed in a liquid electrolyte consisting of 1 mole/liter of $LiClO_4$ in propylene carbonate and cooled down to room temperature, thereby obtaining a flame retardant solid electrolyte containing 70 wt % of the liquid electrolyte and 30 wt % of the polymer. This flame retardant non-ion conductive polymer containing the electrolyte had a conductivity of $2 \times 10^{-3}$ S/cm.

The flame retardance of the solid electrolyte was evaluated in the same manner as in Example 1, revealing that the retardance corresponded to V-1.

EXAMPLE 7

A phosphorus-bearing compound of the afore-indicated formula (X) and acrylonitrile were mixed at a mixing ratio by weight of 25:75, to which azobisisobutyronitrile was added, followed by solution polymerization at 50° C. to obtain a copolymer having flame retardance-imparted moieties therein. 70 wt % of a liquid electrolyte consisting of 1 mole/liter of supporting electrolyte, $LiBF_4$, in a mixed solvent of ethylene carbonate and $\gamma$-butyrolactone at a mixing ratio of 50:50 was added to the polymer, followed by mixing under heating conditions at 100° C. The resultant solution was applied onto a glass sheet where it was cooled down to room temperature. Thus, a solid electrolyte made of the non-ion conductive polymer containing the 70 wt % of the liquid electrolyte was obtained.

The flame retardant solid electrolyte was found to have a conductivity of $3 \times 10^{-3}$ S/cm. The solid electrolyte was evaluated in the same manner as in Example 1 with respect to the flame retardance, revealing that the retardance corresponded to V-1.

EXAMPLE 8

A Br-bearing compound of the afore-indicated formula (II) and vinylidene fluoride monomer were used. Initially, the compound of the formula (II) was dissolved in toluene along with benzoyl peroxide, followed by further introduction of vinylidene fluoride so that a mixing ratio by weight was 30:70 to obtain a copolymer. 70 wt % of a liquid electrolyte consisting of 1 mole/liter of $LiBF_4$ in a mixed solvent of ethylene carbonate and $\gamma$-butyrolactone at a mixing ratio of 50:50 was added to 30 wt % of the polymer. The resultant mixture was mixed and heated at 70° C. The mixture was cooled down to room temperature on a glass sheet to obtain a solid electrolyte containing 70 wt % of the liquid electrolyte.

The solid electrolyte had a conductivity of $3 \times 10^{-3}$ S/cm. The flame retardance of this solid electrolyte was evaluated in the same manner as in Example 1, revealing that the retardance corresponded to V-1.

EXAMPLE 9

A mixture of a bromine-bearing compound of the afore-indicated formula (IV) and a compound of the afore-indicated formula (XIV) at a mixing ratio by weight of 50:50, and acrylonitrile monomer were mixed at a mixing ratio by weight of 40:60. The mixture was treated in the same manner as in Example 2 to obtain a flame retardant solid electrolyte.

The solid electrolyte had a conductivity of $1 \times 10^{-3}$ S/cm. The flame retardance of this solid electrolyte was evaluated in the same manner as in Example 1, revealing that the retardance corresponded to V-0.

COMPARATIVE EXAMPLE 3

The general procedure of Example 1 was repeated without use of any bromine-bearing compound. The flame retardance was evaluated in the same manner as in Example 1, revealing that the solid electrolyte did not pass the standard HB and no flame retardance was shown.

As will be apparent from the foregoing, the flame retardant solid electrolyte of the invention comprises an ion conductive or non-ion conductive polymer matrix having the moieties derived from halogen or phosphorus-bearing compounds and capable of imparting flame retardance to the polymer matrix. The polymer matrix shows good flame retardance. When the solid electrolyte is used in cells where a great current passes within a short time owing to short-circuiting, the ignition of the polymer matrix is suppressed.

The solid electrolyte is also effective in flame retardance when applied to cells using active substances other than lithium, lithium alloys and carbon materials.

What is claimed is:

1. A flame retardant solid electrolyte comprising:
   an ion conductive polymer matrix having moieties derived from a halogen or phosphorus-bearing polymer and capable of imparting flame retardance to said polymer matrix; and
   an electrolyte salt dispersed in said polymer matrix;
   wherein said ion conductive polymer matrix consists of a crosslinked product between a polymer of a first at least one compound selected from the group consisting of alkylene oxides and glycidyl ethers, which polymer is modified with a crosslinkable multiple bond group at part or all of terminal end groups and at functional groups in a polymer chain; and a second at least one compound selected from the group consisting of a compound represented by formula (1), (2) and (3):

(1)

wherein $R_1$ represents a halogen-containing aliphatic hydrocarbon residue, a halogen-containing aromatic hydrocarbon residue, or R' $OR_1$', in which R' represents an aliphatic or aromatic hydrocarbon residue, and $R_1$' represents a halogen-containing aliphatic or aromatic hydrocarbon residue, $R_2$ represents H or $CH_3$, and n is an integer of 1 to 3;

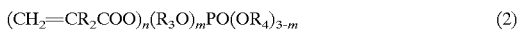 (2)

wherein $R_2$ has the same meaning as defined above, $R_3$ represents an aliphatic or aromatic hydrocarbon residue, $R_4$ represents hydrogen, an aliphatic or aromatic hydrocarbon residue or a phosphorus-bearing aliphatic or aromatic hydrocarbon group, m is an integer of 1 to 3, and n is an integer of 1 to 3; and

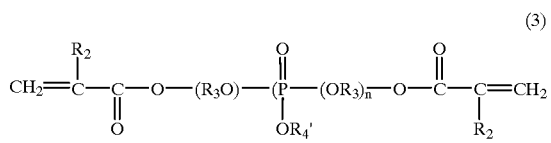 (3)

wherein $R_2$ has the same meaning as defined above, $R_3$ has the same meaning as defined in (2), $R_4$' represents hydrogen, an aliphatic or aromatic hydrocarbon residue, or $—(R_3O)_{m'}—R_5$, in which $R_3$ is as defined above, and $R_5$ represents hydrogen, or an aliphatic or aromatic hydrocarbon residue, and m' is an integer of from 0 to 20.

2. A flame retardant solid electrolyte according to claim 1, wherein said polymer consists of a homopolymer of at least one compound selected from the group consisting of alkylene oxides and glycidyl ethers.

3. A flame retardant solid electrolyte according to claim 1, wherein said polymer consists of a copolymer of compounds selected from the group consisting of alkylene oxides and glycidyl ethers.

4. A flame retardant solid electrolyte according to claim 1, wherein the second at least one compound includes the compound represented by formula (I);

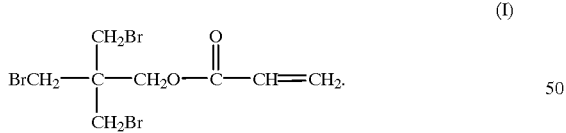 (I)

5. A flame retardant solid electrolyte according to claim 1, wherein the second at least one compound includes the compound represented by formula (II);

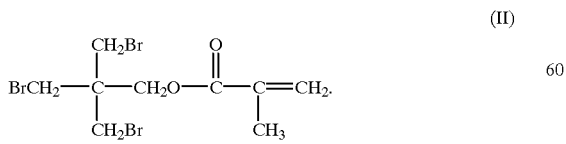 (II)

6. A flame retardant solid electrolyte according to claim 1, wherein the second at least one compound includes the compound represented by formula (III);

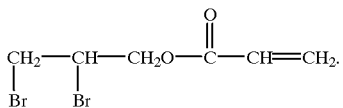 (III)

7. A flame retardant solid electrolyte according to claim 1, wherein said multiple bond group is selected from the group consisting of an acrylic acid group, an acryloyl group and a methacryloyl group.

8. A flame retardant solid electrolyte according to claim 1, wherein said crosslinked product is obtained by irradiation of UV light, an electron beam or a γ-ray or by application of heat.

9. A flame retardant solid electrolyte according to claim 1, wherein said polymer and the second at least one compound are present at a mixing ratio by weight of 40:60 to 98:2.

10. A flame retardant solid electrolyte according to claim 1, wherein said electrolyte salt consists of a combination of a lithium cation and at least one anion selected from the group consisting of $BF_4$, $PF_6$, $ClO_4$, $AsF_6$, $CF_3SO_3$, $N(CF_3SO_2)_2$, $N(C_2F_5SO_2)_2$, $C(CF_3SO_2)_3$ and derivatives thereof.

11. A flame retardant solid electrolyte according to claim 1, further comprising a solvent dissolving said electrolyte salt therein to provide a liquid electrolyte, and said liquid electrolyte is dispersed in said polymer matrix.

12. A flame retardant solid electrolyte according to claim 11, wherein said solvent consists of a non-aqueous solvent selected from the group consisting of carbonates, lactones, ethers, sulfolanes, dioxolanes and mixtures thereof.

13. A flame retardant solid electrolyte according to claim 11, wherein said liquid electrolyte is present at a ratio by weight, to said polymer matrix, of 90:10 to 10:90.

14. A lithium secondary cell comprising the solid electrolyte defined in claim 1.

15. A flame retardant solid electrolyte comprising:
a non-ion-conductive polymer matrix having moieties derived from a halogen or phosphorus-bearing compound and capable of imparting flame retardance to said polymer matrix; and
a liquid electrolyte comprising an electrolyte salt dissolved in a solvent therefor, said liquid electrolyte being dispersed in said polymer matrix;
wherein said non-ion-conductive polymer matrix consists of a copolymer obtained by crosslinking reaction between a copolymerizable monomer and at least one compound selected from the group consisting of a compound represented by formula (1), (2) and (3):

 (1)

wherein $R_1$ represents a halogen-containing aliphatic hydrocarbon residue, a halogen-containing aromatic hydrocarbon residue, or R' $OR_1$', in which R' represents an aliphatic or aromatic hydrocarbon residue, and $R_1$' represents a halogen-containing aliphatic or aromatic hydrocarbon residue, $R_2$ represents H or $CH_3$, and n is an integer of 1 to 3;

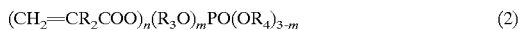 (2)

wherein $R_2$ has the same meaning as defined above, $R_3$ represents an aliphatic or aromatic hydrocarbon residue, $R_4$ represents hydrogen, an aliphatic or aromatic hydrocarbon residue or a phosphorus-bearing aliphatic or aromatic hydrocarbon group, m is an integer of 1 to 3, and n is an integer of 1 to 3; and

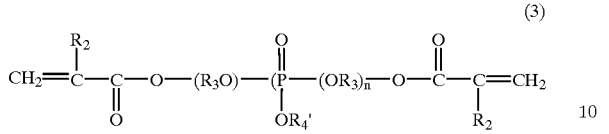
(3)

wherein $R_2$ has the same meaning as defined above, $R_3$ has the same meaning as defined (2), $R_4'$ represents hydrogen, an aliphatic or aromatic hydrocarbon residue, or $-(R_3O)_{m'}-R_5$, in which $R_3$ is defined above, and $R_5$ represents hydrogen, or an aliphatic or aromatic hydrocarbon residue, and m' is an integer of from 0 to 20.

16. A flame retardant solid electrolyte according to claim 1, wherein said at least one compound includes the compound represented by formula (I);

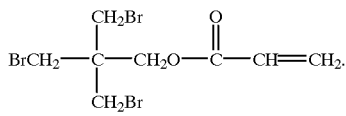
(I)

17. A flame retardant solid electrolyte according to claim 15, wherein said at least one compound includes the compound represented by formula (II);

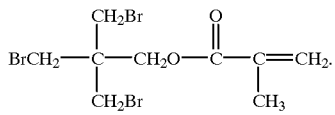
(II)

18. A flame retardant solid electrolyte according to claim 15, wherein said at least one compound includes the compound represented by formula (III);

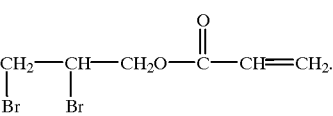
(III)

19. A flame retardant solid electrolyte according to claim 15, wherein said copolymerizable monomer consists of at least one member selected from the group consisting of vinylidene chloride, acrylonitrile and methyl methacrylate.

20. A flame retardant solid electrolyte according to claim 15, wherein said at least one compound is present in an amount of 2 to 60 wt % in said non-ion-conductive polymer matrix.

21. A flame retardant solid electrolyte according to claim 15, wherein said electrolyte salt consists of at least one combination of a lithium cation and at least one anion selected from the group consisting of $BF_4$, $PF_6$, $ClO_4$, $AsF_6$, $CF_3SO_3$, $N(CF_3SO_2)_2$, $N(C_2F_5SO_2)_2$, $C(CF_3SO_2)_3$ and derivatives thereof.

22. A flame retardant solid electrolyte according to claim 15, wherein said solvent is selected from the group consisting of carbonates, lactones, ethers, sulfolanes, dioxolanes and mixtures thereof.

23. A flame retardant solid electrolyte according to claim 15, wherein said liquid electrolyte is present at a ratio by weight, to said polymer matrix, of 90:10 to 10:90.

24. A lithium secondary cell comprising the flame retardant electrolyte defined in claim 15.

* * * * *